United States Patent [19]

DeLisi et al.

[11] Patent Number: 5,495,423
[45] Date of Patent: Feb. 27, 1996

[54] GENERAL STRATEGY FOR VACCINE AND DRUG DESIGN

[75] Inventors: Charles DeLisi, Boston, Mass.; James L. Cornette, Ames, Iowa; Ugur Sezerman, Boston, Mass.; Rakefet Rosenfeld, Boston, Mass.; Sandor Vajda, Boston, Mass.

[73] Assignee: Trustees of Boston University, Boston, Mass.

[21] Appl. No.: 142,597

[22] Filed: Oct. 25, 1993

[51] Int. Cl.⁶ ............................................. G06F 17/50
[52] U.S. Cl. ........................................ 364/496; 364/578
[58] Field of Search .................................. 364/496, 578, 364/497–499; 434/278, 279, 298

[56] References Cited

U.S. PATENT DOCUMENTS

| | | | |
|---|---|---|---|
| 4,704,692 | 11/1987 | Ladner | 364/496 |
| 4,881,175 | 11/1989 | Ladner | 364/496 |
| 4,908,773 | 3/1990 | Pantoliano et al | 364/496 |
| 4,939,666 | 7/1990 | Hardman | 364/496 |
| 5,025,388 | 6/1991 | Cramer, III et al. | 364/496 |
| 5,223,409 | 6/1993 | Ladner et al. | 435/69 |
| 5,241,470 | 8/1993 | Lee et al. | 364/413.15 |
| 5,307,287 | 4/1994 | Cramer, III et al. | 364/496 |
| 5,331,573 | 7/1994 | Balaji et al. | 364/578 |
| 5,434,796 | 7/1995 | Weininger | 364/496 |

OTHER PUBLICATIONS

M. A. Saper, et al. "Refined Structure of the Human Histocompatibility Antigen HLA–A2 at 2.6 ÅResolution" *Journal of Molecular Biology* 219:277–319 (1991).

France Latron, et al. "Positioning of a peptide in the cleft of HLA–A2 by complementing amino acid changes" *Proc. Natl. Acad. Sci. USA* 88:11325–11329 (1991).

David Eisenberg, et al. "Solvation energy in protein folding and binding" *Nature* 319:199–203 (1986).

Joseph A. Ippolito, et al. "Hydrogen Bond Stereochemistry in Protein Structure and Function" *Journal of Molecular Biology* 215:457–471 (1990).

Timothy J. Richmond, "Solvent Accessible Surface Area and Excluded Volume in Proteins" *Journal of Molecular Biology* 178:63–89 (1984).

T. P. J. Garrett, et al. "Specificity pockets for the side chains of peptide antigens in HLA–Aw68" *Nature* 342:692–696 (1989).

P. J. Bjorkman, et al. "Structure of the human class I histocompatibility antigen, HLA–A2" *Nature* 329:506–518 (1987).

Ronald N. Germain "The second class story" *Nature* 353:605–607 (1991).

Olaf Rötzschke, et al. "Naturally–occurring peptide antigens derived from the MHC class–I–restricted processing pathway" *Immunology Today* 12:447–455 (1991).

Bernard R. Brooks, et al. "CHARMM: A Program for Macromolecular Energy, Minimization, and Dynamics Calculations" *Journal of Computational Chemistry* 4:187–217 (1983).

Charles DeLisi, et al. "T–cell antigenic sites tend to be amphipathic structures" *Proc. Natl. Acad. Sci. USA* 82:7048–7052 (1985).

R. Rosenfeld, et al., "Computing the Structure of Bound Peptides" *J. Mol. Biol.* 234:515–521 (1993).

U. Sezerman, et al., "Toward computational determination of peptide–receptor structure" *Protein Science* 2:1827–1843 (1993).

*Primary Examiner*—James P. Trammell
*Assistant Examiner*—Kyle J. Choi
*Attorney, Agent, or Firm*—Baker & Botts

[57] ABSTRACT

A method for computing the conformation and location that a protein fragment will obtain in binding to the active site of a receptor is provided. The invention relates to both the computation of conformation and location of natural ligands within an active site and the design of artificial ligands with useful binding characteristics.

17 Claims, 10 Drawing Sheets

GENERAL STRATEGY FOR VACCINE AND DRUG DESIGN

This invention was made with government support under AI 305 35 02 awarded by the National Institutes of Health. The Government has certain rights in the invention.

FIELD OF THE INVENTION

The present invention relates to a method for vaccine and drug design. The method involves computing optimal ligand configurations and positions within receptor active sites. The method provides a basis for design of ligands with enhanced binding characteristics, useful for rational drug design.

DESCRIPTION OF THE PRIOR ART

Intercellular communication and the various responses of biologically active cells are modulated and controlled by the interaction of ligands with receptors. A predictive understanding of such interactions is important in manipulating normal and pathological cellular behavior. Such an understanding can lead to rational drug and vaccine design strategies.

Several docking strategies of varying degrees of sophistication and computational complexity have been developed and are described in the prior art. Previous methods for computing the location of a ligand within a receptor active site have generally required a fixed structure for the ligand and the receptor. The large computational requirements to compute energies of molecular structures limit the models to purely geometric considerations or to computation of potential fields due to receptor atoms in the region of the active site that do not provide for movement of receptor atoms. Rigid body docking (RBD) operates on the assumption that the receptor and ligand structures are known, and it thus reduces the problem to a six-dimensional search over translational and rotational degrees of freedom [See, Kuntz, I. D., *Science* 257: 1078–1082 (1992); Shoichet, B. K., et al., *J. Mol. Biol.* 221: 327–346 (1991)]. In RBD, the binding position is found by optimizing a target function that involves factors such as surface complementarity, surface area burial, stearic hindrance, electrostatic interaction energy, and solvation free energy.

Semi-flexible docking (SFD) augments the RBD search by local energy minimization of the backbone and side chain conformation of both ligand and receptor at each sampled position in the six-dimensional search space [See, Wodak, S. J., et al., *J. Mol. Biol.* 124: 323–342 (1978)]. The target function in these procedures is usually the potential energy of the complex, based on a molecular mechanics energy function. With a generally available potential function, the SFD approach has some advantage over the simpler evaluation methods.

The most general strategy, flexible docking (FD), minimizes the energy by simultaneously exploring the six rigid body degrees of freedom and the full conformational space of the molecules [See, Goodsell, D. S., et al., *Proteins* 8: 195–202 (1990)]. Such calculations generally involve Monte Carlo strategies, and are effective only for very small ligands. Computational efficiency can be improved by an approximation that decouples the conformational and positional search by an initial exploration of the receptor site using an RBD strategy to select regions of interest, followed by an SFD or FD method on the selected regions [Caflisch, A., et al., *Proteins* 13: 223–230 (1992)]. By spreading the range of starting conformations to a likely subset of possibilities, the combination can provide better sampling, but even this modification does not yield adequate results.

Each of these strategies is useful within certain limits. The RBD approach is most useful for screening a large number of putative ligands, usually small and relatively rigid molecules, for known protein receptors. The SFD approach is potentially useful for determining the structures of unsolved protein-protein complexes when the crystallographic conformation of each molecule in isolation is available. The Monte Carlo based FD approach is required when reliable information about the ligand conformation is lacking, but has serious computational limitations for peptide sizes of immunological interest.

These and other disadvantages of the prior art are overcome by the present invention. The present invention overcomes the prior art limitations and allows for flexing of ligand and even assembly of ligand during the search for optimal configuration and location within a receptor binding region.

SUMMARY OF THE INVENTION

In accordance with the present invention, a method for computing the conformation and location that a protein fragment will obtain in binding to the active site of a receptor is provided. The invention relates to both the computation of conformation and location of natural ligands within an active site and the design of artificial ligands with useful binding characteristics.

It is an object of the present invention to provide a method for computing the conformation of a ligand and location of the ligand in the binding region of another molecule such as a protein or polynucleotide.

It is further an object of the present invention to provide a method for modeling the physical properties of a binding site in a receptor molecule for determining locations and conformations of amino acids in their lowest energy configurations within the binding site, comprising the steps of establishing X, Y, and Z coordinate axes for the receptor molecule to be modeled so that a rectangular region is established with sides parallel to the coordinate axes with the origin of the axes lying in the binding site of the receptor molecule; establishing a grid in the X, Y, and Z coordinate axes with a grid mesh size of sufficient resolution to distinguish low-energy amino acid locations in the binding site; scanning the binding site by placing a model amino acid at each grid point and determining the interaction energy between the amino acid and the binding site and storing in a memory that location and energy; and selecting for each amino acid the lowest energy positions in the binding site as defining the binding site for the amino acid.

It is further an object of the present invention to provide the method for modeling the physical properties of a binding site wherein the scanning step further comprises the steps of prescreening the grid locations in the binding site by determining an electrostatic interaction energy between the amino acid and receptor at each grid location and amino acid orientation; deleting the isolated low electrostatic interaction energy locations and orientations; and determining at the remaining low electrostatic interaction energy positions the amino acid-receptor configuration of lowest energy using a total potential energy process.

It is further an object of the present invention to provide a method for modeling the minimum energy conformation of a ligand within the binding site of a receptor molecule, comprising the steps of establishing X, Y, and Z coordinate axes for the receptor molecule to be modeled so that a rectangular region is established with sides parallel to the coordinate axes with the origin of the axes lying in the binding site of the receptor molecule; establishing a grid in the X, Y, and Z coordinate axes with a grid mesh size of sufficient resolution to distinguish low-energy amino acid locations in the binding site; retrieving previously established X, Y, and Z coordinate axes for the receptor molecule and grid in the X, Y, and Z coordinate axes; retrieving previously established low-energy amino acid configurations within the binding site; selecting a ligand anchor pair from among the low-energy amino acid configurations consistent with the amino acid sequence of the ligand; completing the ligand structure by closing a loop between the ligand anchor pair with amino acid residues using a loop closure process; and determining a minimum energy configuration as defining the conformations of the ligand within the receptor binding site using a molecular modeling process allowing both the ligand atoms and the receptor atoms to adjust.

It is further an object of the present invention to provide the method further comprising the steps of selecting additional ligand anchor pairs for alternate low-energy positions and alternate amino acids within the ligand; closing a loop between ligand pairs; determining a minimum interaction energy for the ligand model so constructed; and selecting from all of the model ligands so constructed a model configuration of lowest total energy and storing the configuration of ligand and receptor in memory.

It is further an object of the present invention to provide a method for modeling the physical properties of a binding site in a receptor molecule and determining the locations and conformations of end-residues of a ligand that binds to the receptor comprising the steps of establishing X, Y, and Z coordinate axes for the receptor molecule to be modeled so that a rectangular region is established with sides parallel to the coordinate axes with the origin of the axes lying in the binding site of the receptor molecule; establishing a box, A, surrounding the probable location of the amino terminus of the ligand and a box, C, surrounding the probable location of the carboxy terminus of the ligand; placing at random positions in box A copies of a model of the amino terminus ligand residue and placing in box C copies of a model of the carboxy terminus of the ligand; minimizing energy by a multi-copy mean-field approximation of the collection of amino termini located in box A by simultaneously moving all the charged end amino acid residue copies within box A until each copy obtains a minimum energy location; grouping the copies of the amino terminus into clusters of similar location and configuration; minimizing energy by a multi-copy mean-field approximation of the collection of carboxy termini located in box C by simultaneously moving all the charged end carboxy residue copies within box C until each copy obtains a minimum energy location; grouping copies of the carboxy terminus into clusters of similar location and configuration; selecting a representative of the amino terminus from the largest cluster in box A as defining the location and configuration of the amino terminus of the ligand; selecting a copy of the carboxy terminus from the largest cluster in box C as defining the location and configuration of the carboxy terminus of the ligand; and storing the selected locations and configurations for the amino terminus and carboxy terminus.

It is further an object of the present invention to provide the method for modeling the minimum energy conformation of a ligand within the binding site of a receptor molecule, comprising the steps of establishing X, Y, and Z coordinate axes for the receptor molecule to be modeled so that a rectangular region is established with sides parallel to the coordinate axes with the origin of the axes lying in the binding site of the receptor molecule; retrieving previously established low-energy end-residues for the amino terminus and carboxy terminus within the binding site; completing the ligand chain structure by closing a loop between the end-residues with models of amino acid residues corresponding to the ligand using torsion angles corresponding to the expected conformation of the ligand and scaling bond lengths to make the intervening chain of correct length to reach between the two end-residues; randomly generating a set of similar loops with torsion and bond angles randomly perturbed from that of the previously constructed chain; minimizing energy by a multi-copy mean-field approximation of the collection of model ligands by simultaneously moving all of the ligands and rescaling the bond lengths to reach known covalent bond lengths; grouping the collection of ligands into clusters of similar location and configuration; and selecting from the largest cluster a representative defining the predicted ligand structure.

These and other advantages of the present invention will become apparent from the following detailed description.

BRIEF DESCRIPTION OF THE DRAWINGS

For a more complete understanding of the invention and the objects and advantages thereof, reference is now made to the following description taken in connection with the accompanying drawings in which like reference numbers indicate like features and wherein:

FIG. 8 depicts the docking of amino-terminal glycines and carboxyl-terminal leucines to the A and F pockets of HLA-A2.

DETAILED DESCRIPTION OF THE INVENTION

Figure 1:
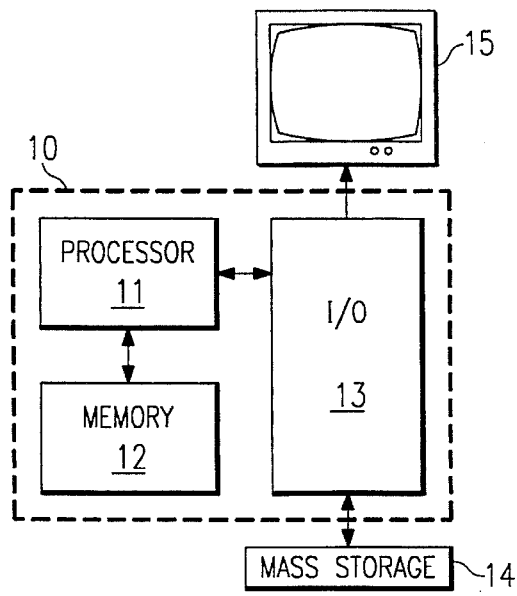
FIG. 1 depicts a representative system for determining the structure of ligands and associated receptors.

The present invention is for a computer aided design and docking of ligands to receptors. "Ligands" include, but are not limited to, "docking peptides," "peptides," drugs, therapeutic agents, polynucleotides or other molecules commonly recognized in the art that bind to receptors. The phrase "docking peptides" or "peptide" as used herein refers to oligopeptides of about 2 to about 25, and preferably about 5 to about 15 amino acid residues in length. The term "receptor" as used herein refers to proteins such as, but not limited to major histocompatibility complex (MHC) proteins, or other receptors involved in immunologic, endocrine, or genomic regulation or drug transport. Such receptors include, but are not limited to immunoglobins, T-cell receptors, estrogen receptors, progesterone receptors, drug binding proteins such as, but not limited to albumin, alpha-1 antitrypsin, and enzymes that catalyze reactions by binding to one or more substrate molecules.

The approximate atomic coordinates of the receptor are assumed to be known, either from direct crystallographic studies or by a perturbational calculation which begins by using the known structure of a closely homologous molecule as the starting point. The crystallographic structure may be obtained through any of the classical techniques for assessing crystallographic structure. Many such structures are obtainable through protein data base files such as, but not limited to, the Brookhaven Protein Data Bank or the European Molecular Biology Laboratory (EMBL) Data Bank. The docking and design problems are then solved by a method of decomposition, analysis and synthesis as follows.

The first step of the method is to find the lowest energy positions and configurations for each of the amino acids of the docking peptide within the binding site of the receptor molecule. The search as described below is computationally intensive, but need be conducted just once for any given receptor molecule. For computational ease, the binding site of the receptor is divided into subvolumes, or regions. The output of the algorithm is a rank ordering, for each of the regions, of the binding propensity of each of the receptor amino acids. Specifically, the output is a matrix, with regions labeling the rows, amino acids labeling the columns, and the elements containing the relative binding energy. This matrix is an amino acid binding energy map of the receptor. The map is developed by minimizing, in seriatim, the energy of each amino acid in each receptor volume element, allowing local movement of the receptor.

Several variants of this procedure are possible. In one, minimization begins with several different alternative configurations of the amino acid under consideration. Multiprocessor capabilities may be utilized by placing different starting positions in different processors. As minimization proceeds, some of them will begin to show similar configurations; i.e., some subset of the initially randomly configured amino acid will begin to converge toward a common structure. Those amino acids that are not part of the structural cluster are eliminated; the remaining similar structures are spread over the empty processors, and minimization, with search for closer clustering continues.

Once a map has been developed, a known peptide can be docked, or a best peptide for that receptor can be designed. Also, molecules containing compounds other than amino acids may be designed for binding to the receptor.

In the abbreviated method, the coordinates of a receptor molecule (MOL) are read from a Protein Data Base (PDB) file and the molecule oriented to a grid containing the active site. For each of 20 amino acids (AA), the binding site of MOL is scanned for favorable AA positions, as follows: (A) each amino acid is placed in various orientations at each grid point and the AA-MOL electrostatic interaction energy for each position (grid location and orientation) is calculated, or (B) the full potential energy is used and locally minimized (rather than just the electrostatic interaction energy being calculated) at each location. The addition of local minimization will increase computer time. On the other hand, addition of local minimization allows AA positions to be chosen sparsely, since the ligand will generally move several Angstroms during minimization.

Those low-energy positions for the AA for which there are also several neighboring positions with similar low energies are selected. This avoids narrowly confined minima in the energy surface that are unlikely to be populated by AA. The AA is placed at each of the selected low-energy positions and the energy of the AA-MOL complex is minimized using all energy terms (this is omitted if option (B) is used). The positions are ranked according to the minimized energies and the best N of about 8 to about 12, and preferably about 10 positions associated with this particular AA are saved.

For a peptide chain which is to be placed in the binding site: (A) two or more amino acids in the peptide which have low-energy positions in the active site are selected as stabilizing residues. The selected positions must be consistent with the amino acid location within the peptide sequence; (B) The backbone between the terminal anchor residues is filled in using the commercially available software CONGEN (Conformation Generator program), manufactured and distributed by Bristol-Myers Squibb Company, to close the intervening loop and to obtain the side chain conformations. For each pair of anchors conformations and spacing that can close a loop, many possible conformations of the intervening chain are obtained. The best four to six, and preferably five (lowest energy) conformations are chosen and stored as representing the receptor conformation.

In the second algorithm, a PDB file is read and the molecule (MOL) oriented to a coordinate system where the Z-axis runs along the binding cleft and the X-axis is perpendicular to the $\beta$-floor of the MOL. For example, for MHC, because the amino terminus residue of the peptide consistently is found in or near the A-pocket and the carboxyl terminus in or near the F pocket of the MHC cleft [Saper, M. A., et al., *J. Mol. Biol.*, 219: 277–319 (1991)], those two pockets are explored first: (A) a 5 Å×5 Å×5 Å box (box A) near and surrounding the hydroxyl groups of the residues tyrosine 171, tyrosine 7 and tyrosine 59 that are conserved among all MHC molecules is located; (B) Ten copies of a $NH_3^+$-residue (the positively charged N-terminus residue) of the peptide are placed (computationally) randomly in box A; (C) The energy of the ten-copy-MHC system is minimized using a multi-copy mean-field approximation. This means that the multiple copies of the residue are transparent to each other, but each feels the full force of the MHC receptor, and the MHC receptor feels the mean-field of the multiple ligands; (D) a 7 Å×5 Å×5 Å box (box F) near residues tyrosine 84, threonine 143 and lysine 146, also conserved among MHC molecules is located, ten copies of a $COO^-$-residue of the peptide are placed randomly in box F, and a multi-copy minimization is used as in step (C).

During minimization, the initially randomly distributed model residues tend to cluster with the larger clusters having lower energy values. From the largest cluster in each pocket, one configuration is selected as the predicted end-residue. A bond-scaling-relaxation loop closure algorithm is used [See,, Qiang, Z., et al., *J. Computational Chemistry*, 14: 556, (1993), expressly incorporated by reference herein], with the multi-copy procedure to locate the remaining seven amino acids of the peptide chain: (A) a set of ten random configurations of the seven amino acid residue chain are generated and each configuration is subsequently scaled to meet the distance constraints defined by the two terminal residues. Because the known instances of peptides binding in the MHC cleft are in an extended conformation, the backbone dihedrals for the ten random configurations are selected randomly from those appropriate to an extended conformation. The equilibrium bond lengths in the energy parameters are scaled accordingly; (B) for each of the ten configurations in (A), a group of ten nearby configurations is generated by relatively small random perturbations of all dihedral angles of the original configuration. Each resulting group of ten candidate peptide configurations is then minimized with the multi-copy mean-field approximation; and (C) as with the terminal residues, the group of candidate peptide configurations tend to cluster and the larger clusters have the lower energies. A member of the group of ten that does cluster and that has lowest energies among the clustering groups is selected as the predicted peptide conformation.

FIG. 1 depicts a representative system for determining the structure of ligands and associated receptors. Shown in FIG. 1 are computer system 10 including processor 11, memory 12, and input/output (I/O) 13. Computer system 10 can be embodied in many forms so long as the system provides sufficient processing power to execute the present system. Computer system 10 can be embodied in a personal computer, work station, or main frame computer. In computer system 10 is processor 11 for controlling and executing the steps for determining the structure of ligands and associated receptors of the present invention. Processor 11 can be embodied in a single processor or multiple processors.

Connected to processor 11 is memory 12 which may be any suitable form of memory typically used in the art to store data and instructions executed by processor 11. Providing connection to system 10 is I/O 13. I/O 13 of the present invention provides the necessary translation of signals between computer system 10 and peripheral devices. Shown in FIG. 1 are examples of two peripheral devices that may be connected to system 10; mass storage 14 and display 15. Mass storage 14 is any data storage system available in the art, including, but not limited to; hard disk drives, floppy disk drives, magnetic disk drives, optical storage, CD ROM, or any PDB. Display 15 is shown connected to system 10 and can be used to display information and data processed by system 10 of the present invention.

It is noted that processor 11, memory 12, and I/O 13 of computer system 10 can be embodied as separate discrete devices, or implemented on a single integrated circuit chip without affecting the inventive concepts of the present invention. In an alternate embodiment to the present invention, computer system 10 is a programmable controller.

Figure 2:
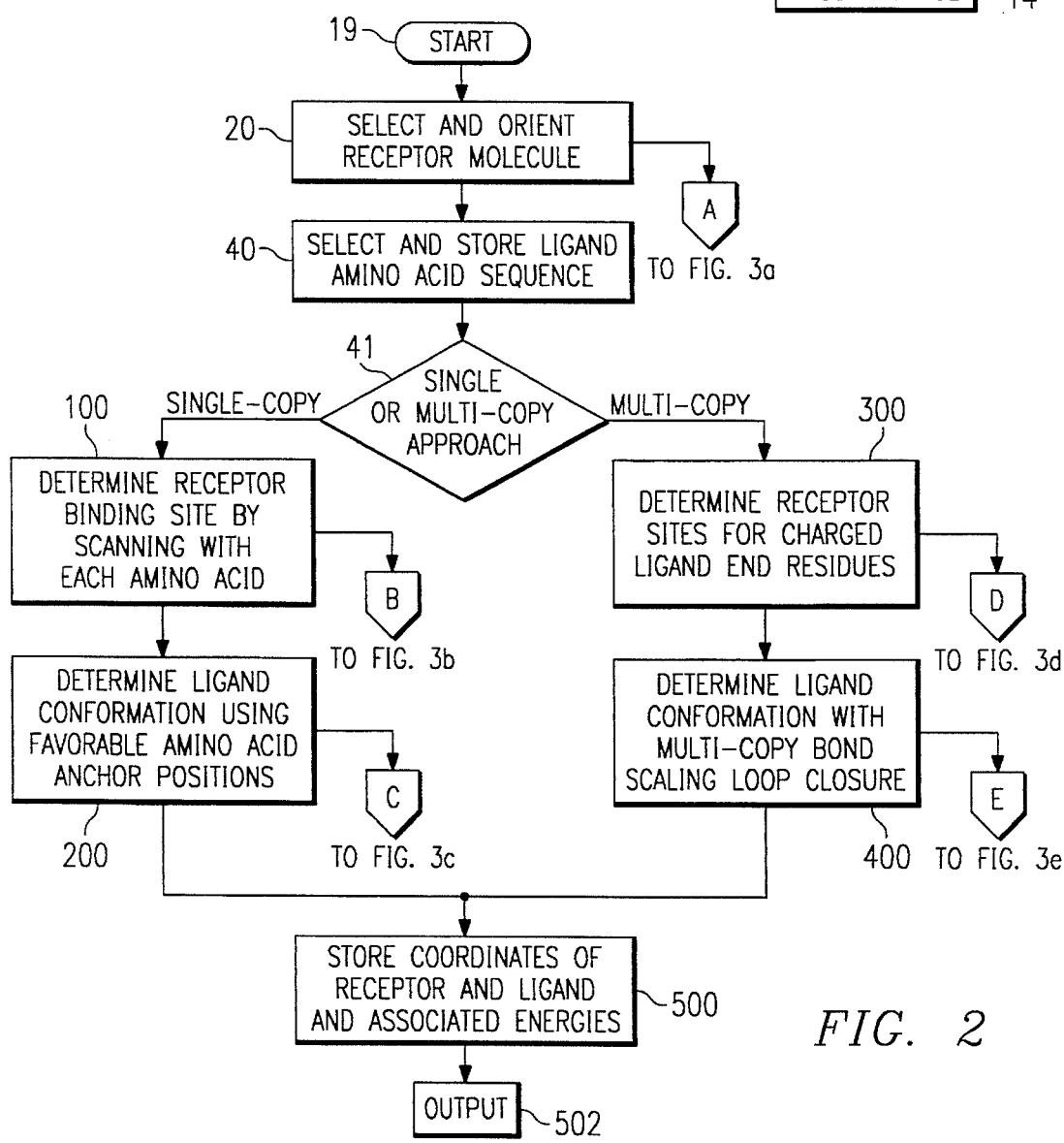
FIG. 2 is a top level flow diagram of the process of the present invention for determining the structure of ligands and associated receptors.

FIG. 2 shows a flow chart of the process of the present invention for determining the structure of ligands and associated receptors. FIG. 2 is a top-level flow chart with additional detail provided in FIGS. 3a through 3e and related discussions. The steps shown in FIGS. 2 and 3a–3e are representative of the steps that are executed by computer system 10 of FIG. 1. The programming of system 10 in performing the modeling system of the present invention can be developed with standard programming techniques which are well known in the art.

In FIG. 2, the present inventive process is initiated at step 19, and at step 20 a receptor molecule is chosen and the representative file of the receptor molecule is retrieved from a data base. Also at step 20, a region of interest (receptor or binding site) of the molecule is identified, and the coordinates of the molecule are translated to align with the binding site. At step 40 an amino acid sequence corresponding to the ligand to be modeled for binding is selected or input into the system. The selected ligand amino acid sequence data is stored in memory 12 or mass storage 14 of computer system 10 (see FIG. 1).

Proceeding to step 41, a query is made as to whether a single or multi-copy approach is desired in the practice of the present inventive method. If a single-copy approach is chosen, the flow proceeds to step 100, where the receptor binding site on the molecule is established. This is accomplished by scanning the receptor binding site with each amino acid from the chosen ligand amino acid sequence (step 40). Once the receptor site is determined, the flow proceeds to step 200 where the conformation of the ligand is determined using the favorable amino acid positions determined in step 100.

If at step 41 a multi-copy approach of the present invention is desired, then the flow proceeds to step 300. At step 300, the locations of all ligands and residues of the multi-copy amino acid sequence are determined. This reveals multiple receptor sites in the chosen receptor molecule. The flow next proceeds to step 400 where the ligand conformations that bind into the molecule's receptor sites are determined (step 300). A multi-copy bond scaling loop closure process is employed to determine the ligand conformation at step 400 of the binding ligands.

Regardless of whether a single-copy or multi-copy approach is taken, the flow proceeds to step 500 wherein the coordinates defining the conformation of the receptor and ligand and associated energies are stored by processor 11 in memory 12 or mass storage 14. Once the receptor and ligands and associated energies are determined by either of the processes identified, then that information may be output by I/O 13 at step 502 or otherwise used as discussed in the examples herein. A computer graphics program Par visualizing chemical structures known as QUANTA, manufactured by Molecular Simulations, Inc. (Waltham, Mass.), has been successfully used in displaying the receptor and ligand conformations determined in the previous steps on display 15, but other similar programs may be used.

Figure 3A:
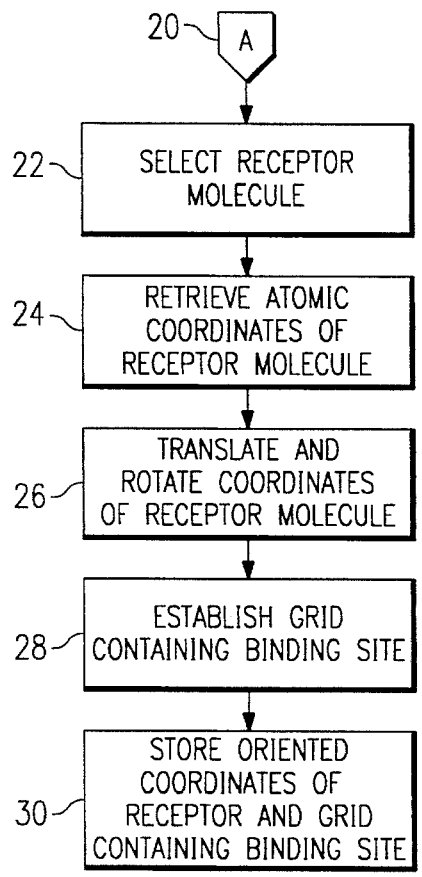
FIGS. 3a through 3e are flow charts showing the steps executed by the present system to determine the structure of ligands and associated receptors.

FIG. 3a shows further detail of the steps executed by system 10 for step 20 of FIG. 2. The receptor molecule is selected at step 22, and in step 24 the chosen molecule is retrieved from memory 12 or mass storage 14. The retrieval of the receptor molecule in step 24 includes the retrieval of the atomic coordinates of the molecule.

In step 26, processor 11 establishes X, Y, and Z coordinate axes for the receptor molecule by translating and rotating its atomic coordinates such that a rectangular region encompassing the binding site is established with sides parallel to the coordinate axes. At step 28, processor 11 establishes a grid in the X, Y, and Z coordinate axes with a mesh size of sufficient resolution to distinguish low-energy amino acid locations within the binding site. At step 30, the oriented coordinates of the receptor, and the grid containing the binding site are stored in memory 12 or mass storage 14.

Returning to FIG. 2, once the receptor molecule has been selected and the new coordinates are established, the flow proceeds to step 40. In step 40 a ligand amino acid sequence is input into system 10. The amino acid sequence makes up the ligand or peptide to be modeled for binding with the chosen receptor molecule. The data representing the ligand amino acid sequence includes the atoms and covalent bonds between atoms is stored by processor 11 in memory 12 or mass storage 14.

At step 41 a query is made as to whether a single or multi-copy of the ligand amino acid sequence will be processed under fine present invention. If a single copy approach is desired, the flow proceeds to step 100, and if a multi-copy approach is desired, the flow proceeds to step 300.

Figure 3C:
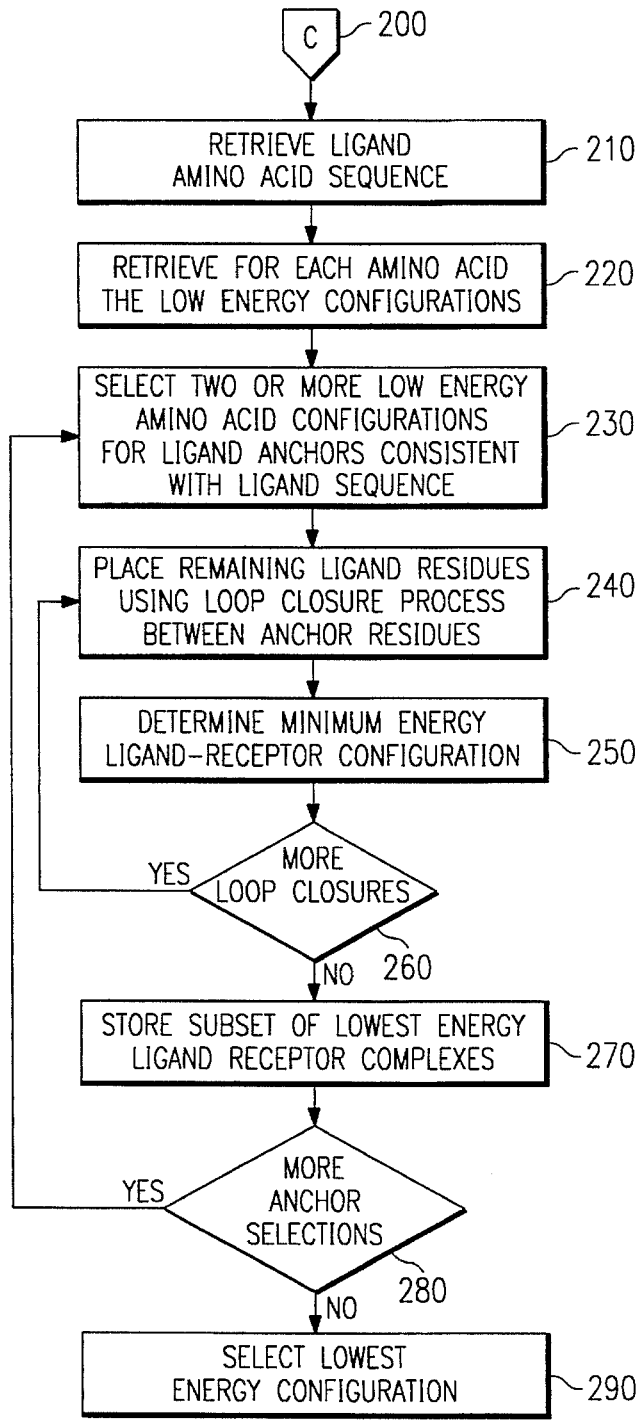
Figure 3B:
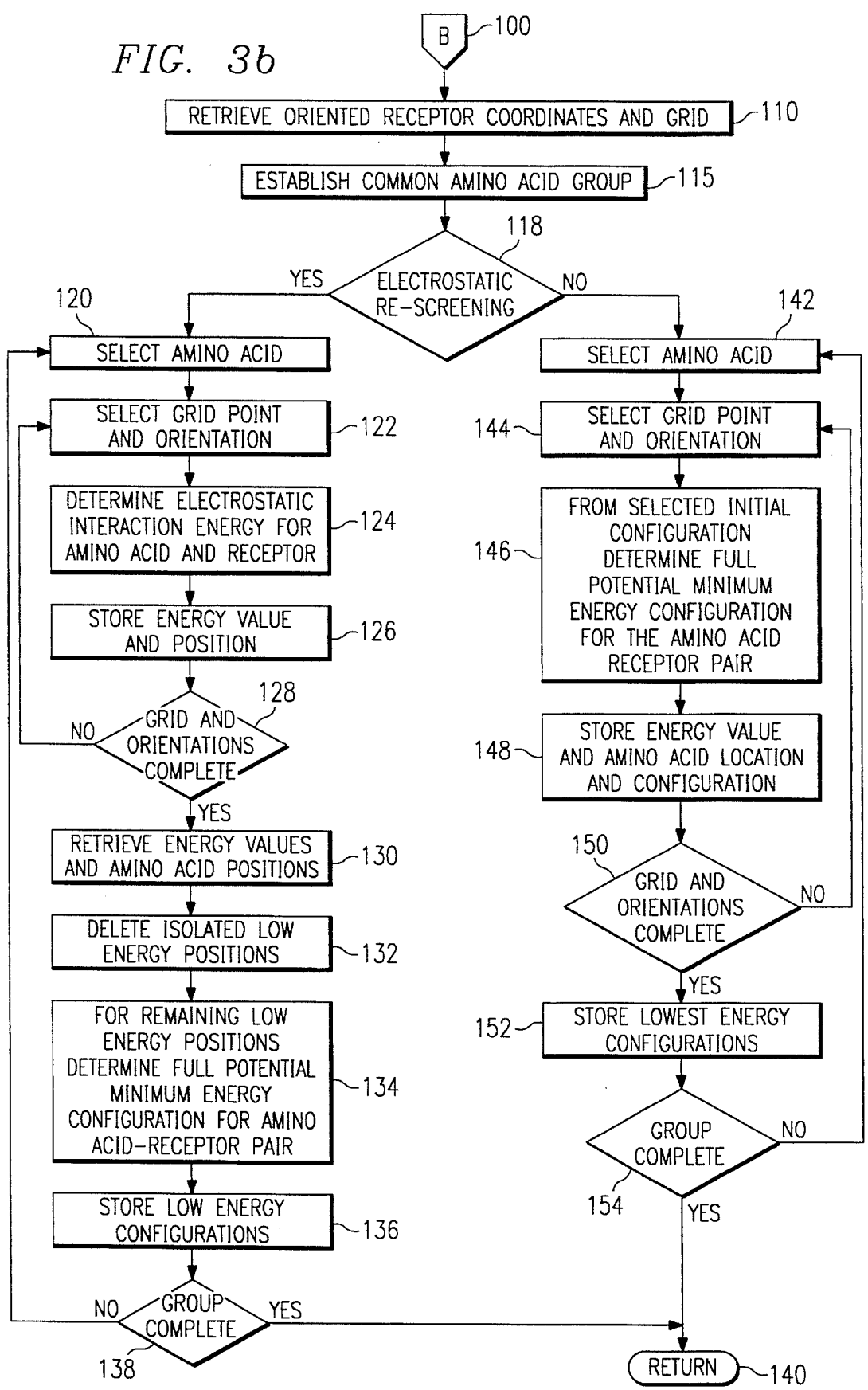

FIG. 3b shows additional detail for step 100 wherein the receptor binding site is determined by scanning the binding site with each amino acid of the ligand amino acid sequence. At step 110 processor 11 retrieves from memory 12 or mass storage 14 the oriented coordinates and grid for the chosen receptor molecule. These are the coordinates and grid established in steps 20 through 30 of FIG. 3a. At step 115 a common amino acid group is established from the amino acid sequence created at step 40. Amino acid groups including 20 members have been successfully used.

At step 118, a query is made as to whether the energy of placement interaction should include electrostatic energy prescreening is desired or whether the full potential energy between the amino acid and receptor molecule should be utilized. If electrostatic energy prescreening is desired, the flow proceeds to step 120, and if electrostatic energy prescreening is not desired the flow proceeds to step 142.

At step 120, one of the amino acids from the amino acid group established in step 115 is selected for scanning in the receptor binding site At step 122 a grid pint and orientation within the binding site is selected, and at step 124 the electrostatic interaction energy for the amino acid is determined. The determined interaction energy is stored by processor 11 in memory 12 or mass storage 14 at step 126. At step 128 a query is made as to whether all the grid points and orientations for the amino acid are complete. If they are not, the flow returns to step 122 the next grid point is ascertained and steps 126 and 128 are repeated.

Once the interaction energy is determined for the amino acid at all of the grid points in the binding site, the flow proceeds to step 130. At step 130, processor 11 retrieves all the energy values and amino acid positions stored in step 126. At step 132, the isolated low-energy positions are deleted leaving a subset of low-energy positions for the amino acid. At step 134, the full potential minimum energy configuration for the amino acid receptor pair is determined. Step 134 includes using the full potential energy between the amino acid in the binding site of the receptor molecule and full internal energy within the amino acid and within the receptor including; electrostatic, Vander Waal's, bond, bond angle, and torsion energies. Processor 11 stores this configuration in memory 12 or mass storage 14 at step 136.

At step 138, a query is made as to whether all the amino acids in the group established at step 115 are complete. If they are not, the flow returns to step 120 where the next amino acid in the group is selected for processing through steps 122 through 136. If all the low-energy configurations for all the amino acids have been determined and stored by processor 11, the flow proceeds to step 140 and returns to FIG. 2. Returning to step 118, if electrostatic prescreening is not desired, the flow proceeds to step 142 where an amino acid form the amino acid group established at step 115 is selected for scanning in the receptor binding site. At step 144, a grid pint and orientation with the binding site is selected, and at step 146 the full potential minimum energy configuration for the amino acid receptor pair is determined. Step 146 determines equivalent data to that determined in step 134. At step 148, processor 11 stores this configuration in memory 11 or mass storage 14.

At step 150, a query is made as to whether all the grid points and orientations for the amino acid are complete. If they are not, the flow returns to step 144, where the next grid point is determined and steps 146 and 148 are repeated.

Once the interaction energy is determined for all the amino acids at all the grid points in the binding site, the flow proceeds to step 152. At step 152, processor 11 stores the lowest interaction energy configurations in memory 12 or mass storage 14. At step 154, a query is made as to whether all the amino acids in the group have been energy minimized. If they have not, the flow returns to step 142 where the next amino acid is selected for processing through steps 144 through 152. If all of the amino acids in the group established at step 115 are complete, the flow proceeds to step 140 and returns to FIG. 2.

Following the completion of all of the steps included in step 100 of FIG. 2, the flow proceeds to step 200 where the ligand structure/conformation is determined, with additional detail for step 200 provided in FIG. 3c. In FIG. 3c at step 210, the ligand amino acid sequence created at step 40 (FIG. 2) is retrieved by processor 11. At step 220, the low-energy configurations for each amino acid in the amino acid sequence stored at step 170 are retrieved. The previously identified low-energy locations within the binding site of the receptor molecule are used to assemble a ligand structure within the binding site. At step 230, two or more low-energy amino acid configurations are selected as ligand anchors (ends) consistent with the ligand sequence.

At step 240, the ligand chain is completed by placing the remaining ligand residues between the ligand anchors using a loop closure process. The backbone between the terminal anchor residues is filled in using the commercially available software CONGEN to close the intervening loop and to obtain the side chain conformations. At step 250, the minimum energy is determined for the ligand-receptor complex for the loop closure established in step 240.

At step 260, a query is made as to whether all of the loop closures for the pair of ligand anchors is complete. If there are additional loop closures, the flow returns to step 240 where the additional loop closures are determined by processor 11. If all loop closures are complete, the flow proceeds to step 270.

At step 270, processor 11 causes the subset of the lowest energy ligand-receptor complexes calculated in step 250 to be stored. At step 280, a query is made as to whether additional anchor pairs exist. If they do, the flow returns to step 230 for processing of the additional anchors. If all anchor pairs have been completed, the flow proceeds; to step 290. At step 290, the lowest energy ligan-receptor configuration is selected. The lowest energy configuration determined at step 290 represents the probable ligand structure for binding to the receptor site determined at step 100. Returning to FIG. 2, at step 500 the coordinates of the receptor, ligand, and their determined energies are stored by processor 11 in memory 12 or mass storage 14. The ligand-receptor, and associated energies may be output at step 502 to a display or used in other suitable matters.

Returning to step 41, if a multi-copy approach to ligand and receptor conformation determination is desired, the flow proceeds to step 300 where the locations and conformations of the binding sites (receptors) for a multi-copy ligand amino acid sequence are determined.

Figure 3D:
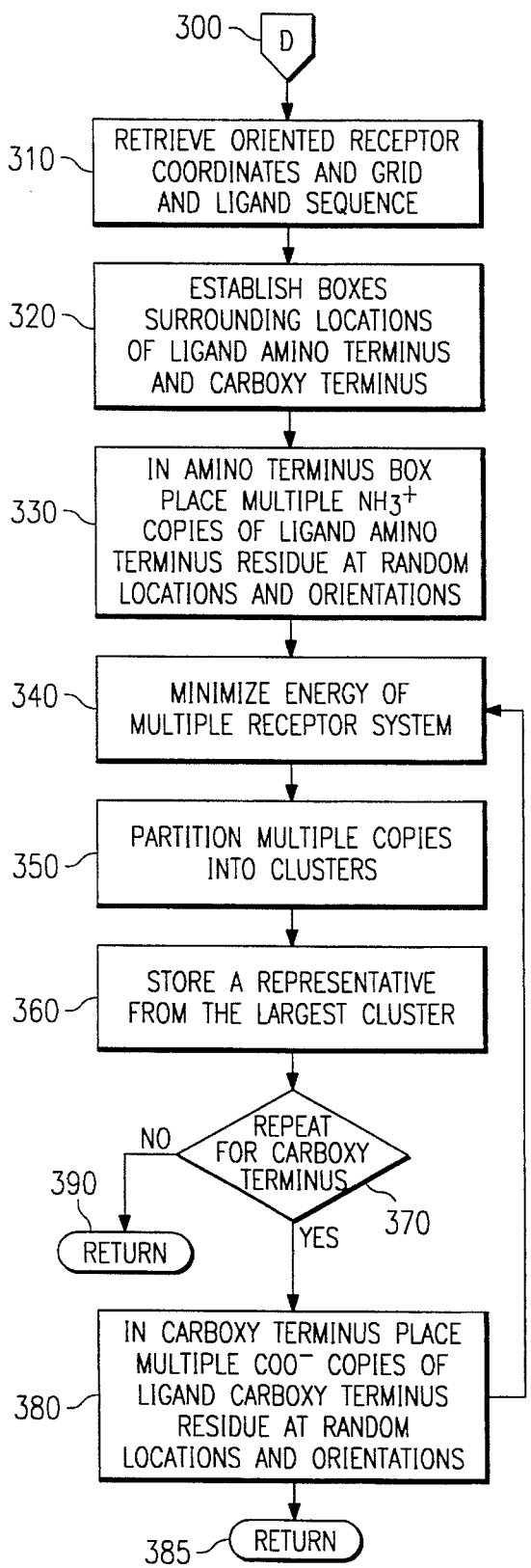

FIG. 3d shows additional detail for determining receptor locations for a multi-copy ligand. At step 310, the oriented receptor coordinates, grid, and ligand amino acid sequence created in steps 20 and 40 are retrieved by processor 11 from memory 12 or mass storage 14. At step 320, processor 11 establishes boxes within the binding sites of the receptor molecule that contain the probable end-residue positions of the ligand amino acid[ sequence. The boxes surround locations of the ligand's amino terminus (end) and carboxyl terminus. At step 330, multiple copies of charged end-residue ($NH_3^+$) are placed in the boxes in random positions and orientations.

At step 340, the minimum energy locations for the charged end-residue is determined using a multi-copy mean-field energy minimization algorithm which simultaneously moves all of the copies of the charged end-residues to minimum energy locations. This means that the multiple copies of the charged end-residues are transparent to each other, but each feels the full force of the receptor, and the receptor feels the mean-field of the multiple ligands. A multi-copy mean-field approximation algorithm found to be acceptable for step 340 has been written as a modification of the software CHARMm manufactured by Harvard University. Molecular modeling software AMBER (Assisted Model Building with Energy Refinement, from the Trustees of the University of California, San Francisco, Calif.) and ECEPP (Empirical Conformational Energy Program for Peptides, from Indiana University) appropriately modified, will perform the multi-copy mean-field energy approximation required for step 340.

At step 350, the multiple copies are grouped into clusters of copies with similar positions and orientations. It is known that the initially randomly distributed charged end-residues tend to cluster, and that the larger clusters have lower energy values. From the largest cluster in each box., a representative cluster is selected as a predicted end-residue.

At step 370 a query is made as to whether to repeat the process of steps 340 through 360 for carboxyl terminus (COO⁻). If not, then the flow proceeds to step 390 where it returns to FIG. 2. If it is desired to repeat steps 340 through 360 for the carboxyl terminus, the flow proceeds to step 380.

At step 380, processor 11 establishes boxes within the binding sites of the receptor molecule and places multiple copies of the ligand carboxyl terminus residue at random locations and orientations. At step 340 through 360, the energy of the carboxyl terminus residue boxes are minimized with a representative from the largest cluster selected as the predicted end-residue at step 360. Once the carboxyl terminus is selected, the flow returns to FIG. 2 at step 385.

Figure 3E:
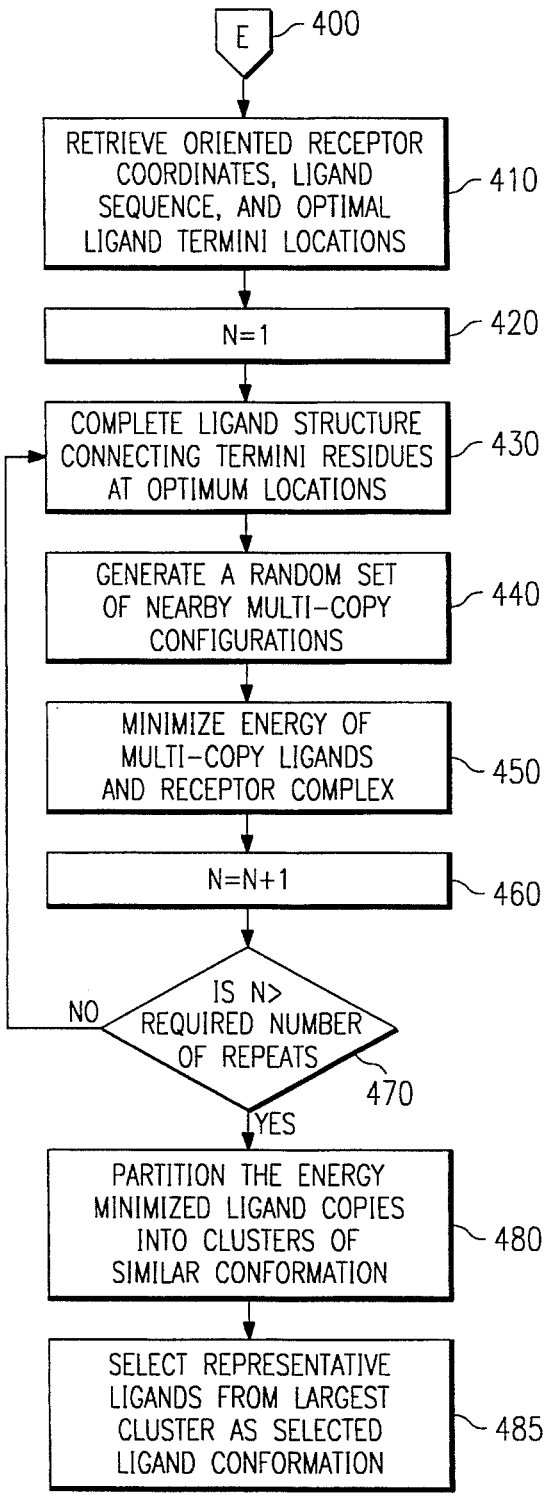

FIG. 3e shows additional detail of step 400 for determining the conformations for a multi-copy ligand amino acid sequence. At step 410, the oriented receptor coordinates (step 20), ligand amino acid sequence (step 40), and optimal ligand termini locations (step 360) are retrieved by processor 11. At step 420, the number of copies in the multi-copy process is initiated at one. At step 430, the first ligand structure is completed by constructing multiple copies of the segment intermediate to the end-residues with bond lengths scaled to fit the distance between the end-residues and backbone torsion angles randomly selected near the values of the expected ligand structure. The ligand structures are completed by connecting termini residues at optimum locations with a bond scaled intermediate chain and randomly selected dihedral angles ,consistent with expected ligand conformation. At step 440 is generated a loop of 10 nearby configurations using small random perturbations of dihedral angles. At step 450 the energy of the 10 copy ligands and receptor complex is minimized using a multi-copy mean-field approximation and bond scaling restoration. This includes simultaneously moving all the ligand copies to standard bond lengths and low-energy configurations within the binding site while holding the end-residues in their computed low-energy position. At step 460, the number of configurations completed is incremented and at step 470 it is compared to the number of multi-copy ligands in the set. If additional candidate ligands are to be computed, then the flow returns to step 430 where steps 430 through 450 are repeated.

If the number of configurations processed equals the number in the set at step 470, then the flow proceeds to step 480 where the energy minimized ligand copies are partitioned into clusters of similar conformation. At step 485, a member of the group of the clusters that has the lowest energy among the clustering groups is selected as the predicted ligand conformation.

The flow now returns to FIG. 2 at step 500 where the data representing coordinates of the multi-copy ligand, receptor, and associated energies are stored by processor 11 in memory 12 or mass storage 14. This data can be used to create a display of the receptor molecule and ligand or otherwise used as appropriate.

The following examples illustrate the teachings of the present invention, but do not limit the scope of the invention.

EXAMPLE 1

Phosphocholine-immunoglobulin Complex

Crystallographic structures have been obtained for phosphocholine, both free and complexed to an McPC 603 Fab fragment. A comparison of the two structures indicates very little change in either structure when phosphocholine binds; i.e. docking is essentially rigid. This example demonstrates the binding of phosphocholine to an immunoglobulin (receptor) complex.

We covered the receptor binding site with a 6×6×6 Å³ grid, allowing 1 Å translational moves, and rotations of 60° about each axis. The electrostatic interaction energy was calculated over the resulting 46,656 points of the six-dimensional space and varied from −423 kcal/mol to 212 kcal/mol. The number of positions was reduced to 233 by retaining only those having an energy below (i.e. more favorable than) a cutoff of −150 kcal/mol, and also having at least 21 of their 26 nearest neighbors with energies below the cutoff. This latter condition removed structures at isolated grid points, so that those remaining form a contiguous region. Subsequent local minimization using the full potential caused an average all-atom RMS change of 0.67 Å in the receptor. The typical RMSD between the observed and calculated structures, obtained without translating or rotating the energy minimized phosphocholine, was less than 0.7 Å.

Figure 4:
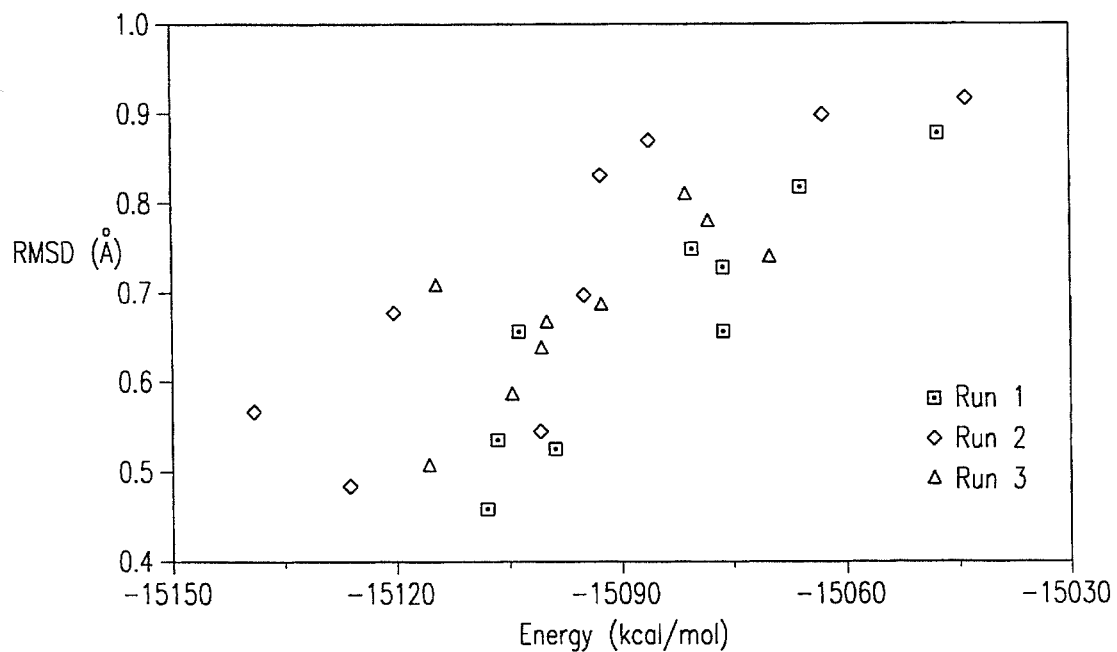
FIG. 4 depicts an all-atom RMS deviation between the calculated and x-ray structures of bound phosphocholine of the Fab-phosphocholine complex.
Figure 5:
FIG. 5 depicts the predicted and crystal phosphocholine conformation.

The center of the 6×6×6 Å³ grid was placed randomly but not further than 1 Å from the center of mass of the phosphocholine in its crystallographically determined position. Thus, the most distant positions on the grid (i.e., the most distant potential positions for the center of mass of the ligand) were slightly more than 5 Å away from the center of mass in the x-ray structure. For comparison, the deviations between the two centers of mass were below 0.3 Å for all low-energy conformations. In order to assess the sensitivity of the final results to the grid location, and to avoid a spurious conformational search that might result from atomic positions falling at grid points, the entire calculation was repeated three times with randomly placed grids. The five lowest energies ($E_c$) varied between −15,118 kcal and −15,139 kcal, with some variation in RMSD at a given $E_c$ (FIG. 4), and with 7 conformations at approximately 0.6 Å RMSD from the crystal structure. The 27 points represent the results of nine different minimizations for each of three grid placings identified by the different characters. The lowest energy complex in this group superimposed on the crystal structure is shown in FIG. 5.

The main binding contributions were from Arg-52, Ash-53, and Tyr-102 on the heavy chain; and Asp-97, Ser-99, and Asn-96 on the light chain. Tyr-33 and Tyr-100 were hydrogen bond stabilized in a location such that, together with Arg-52, they formed an energetically favorable pocket for the phosphocholine phosphate group.

EXAMPLE 2

Enzyme-dipeptide Complexes

This example describes the docking of dipeptides to enzyme active sites.

Three different crystallized dipeptide systems were investigated, each of which provided a suitable test of the RBD-SFD strategy: Ile-Val and Val-Val, interacting with two variants of the trypsin-trypsinogen inhibitor complex, 3TPI and 4TPI, respectively, which differ at position 15 of the inhibitor; and Tal-Trp interacting with thermolysine. Since the dipeptides were flexible, the calculation was repeated for four different initial conformations of each system. For each calculation approximately 90 peptide conformations remained after the electrostatic prescreen. After further screening by removal of steric clashes, 25–30 conformations typically remained to be minimized in the SFD stage of the algorithm.

For the Ile-Val (3TPI) system, the average RMS change during local minimization was 0.66 Å for the peptide, and 0.32 Å for the receptor. In two conformations of the trypsin-trypsinogen (Ile-Val) complex, the interaction energy was high, but the complex energy was below −8900 kcal/mol. Deleting these structures, the 10 lowest energy conformations had all-atom RMSD from the x-ray structure of less than 1.3 Å. Similar calculations for the other two dipeptide systems yielded similar results.

EXAMPLE 3

Semi-flexible Docking Larger Peptides to Class I MHC Products

This example demonstrates the docking of larger peptides to an MHC receptor.

The region containing the binding site of the class I $D^d$ MHC molecule (residues 1–180) was determined by homologous extension from the x-ray coordinates of the corresponding residues in HLA-A2, which can be optimally aligned to it without insertions or deletions. Nonconserved side chain positions were obtained using the Homology option of the QUANTA modeling software (Polygen Corp., 1990), and a 50-step local minimization was used to allow for minor adjustments in the main chain.

A coordinate system with x-axis oriented along the MHC groove was selected, and y and z-axes perpendicular to the β-sheet and α-helices, respectively, were also selected. The MHC site was covered with a 20×20×10 Å$^3$ parallelepiped with a grid having a 1 Å spacing. Rotation about the x-axis in steps of 60° was unrestricted, while steric clashes restricted rotation about the y and z-axes to 55° in each direction.

Although crystal structures indicate that MHC bound peptides were in extended conformations, an alpha helix was chosen as a starting confirmation in order to explore the extent to which it would change during minimization. Just as with dipeptides, the conformation adjusts during minimization, the lowest energy state being extended, with a kink between residues 322 and 323.

Two residues, Arg-322 and Phe-324, made the dominant contribution to the stability of the complex (Table I).

TABLE I

Total interaction energy for each residue of Peptide-18

| Residue No. | Type | Energy$^a$ | Contact residues on MHC |
|---|---|---|---|
| 322 | Arg | −229 | R155,D156,Y159 |
| 323 | Ala | +7 | — |
| 324 | Phe | −89 | F74,W97,W114,P116 |
| 325 | Val | −21 | |

$^a$CHARMm interaction energy with MHC, kcal/mol.

Arg-322 pointed toward the α-2 domain of the MHC molecule, forming hydrogen bonds at a polymorphic position (156) with Asp, and at a nonpolymorphic position (159) with Tyr. The Ala-323 side chain also pointed toward α-2 but without contacting MHC residues. Phe pointed into the groove, toward Phe-74 on the alpha-helix wall, and toward Trp-97 and Trp-114 on the floor. The fourth ligand residue, Val-325, pointed up, away from the groove, contributing little to stability.

EXAMPLE 4

Oligopeptides: Single Copy Application

Figure 6:
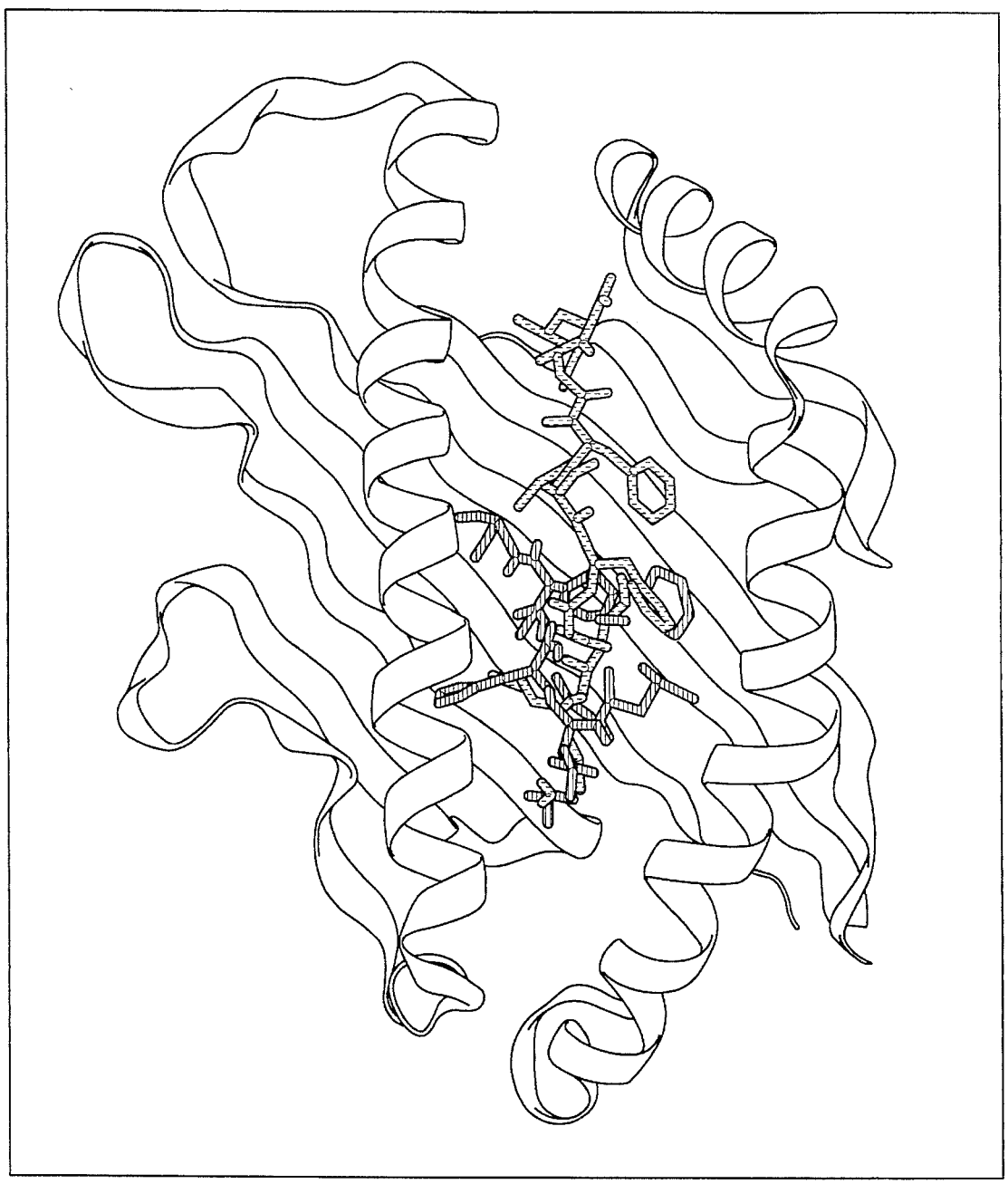
FIG. 6 depicts the predicted conformations of helical and extended M.58-66 binding to HLA-A2.

This example describes the docking of the HLA-A2 influenza A matrix protein (M.58-66) using the single copy approach. The docked location obtained after energy minimization had the matrix peptide displaced only about 0.9 Å from its starting position, with the amino terminus anchored at a pocket that does, in fact, usually accommodate the amino terminus of immunogenic peptides. The carboxyl end was slightly extended, mainly because it found favorable interactions with residues His-70 and His-74. The helical 9-mer was too short to span the MHC positions that anchor the extended nonamer, and hence it tended to be bi-stable, with the correct position for one or the other end. Of the 20 lowest energy positions, 12 were at the amino end of the HLA-A2 groove, including the best four positions, and five were at the carboxyl end. FIG. 6 shows the lowest energy conformation which was at the amino end (Table II) location of the HLA-A2 groove, compared to the extended nonamer.

TABLE II

Total interaction energy for each residue of peptide M.58-66 of the influenza matrix protein in helical conformation

| Residue No. | Type | Energy | Contact residues on MHC |
|---|---|---|---|
| 58 | Gly | −76 | Y7,F33,Y59,E63,K66,W167,Y171 |
| 59 | Ile | 29 | G62,E63,R65,K66,W167 |
| 60 | Leu | −4 | K66,Y159,T163 |
| 61 | Gly | −20 | Y7,K66,Y99,Y159,T163 |
| 62 | Phe | −22 | Y7,F9,M45,E63,K66,H70,Y99 |
| 63 | Val | 4 | Y99,H70 |
| 64 | Phe | −17 | Y99,114,L156,Y159 |
| 65 | Thr | −23 | Y7,F9,H70,Y99 |
| 66 | Leu | −28 | F9,F22,H70,T73,H74,R97,Y99 |

$^a$CHARMm interaction energy with MHC, kcal/mol.

The influenza matrix peptide M.56-68 with tyrosine at position 56 (M.Y57-68) was modeled using the method of the present invention. Table III shows the total interaction energy for each peptide residue. A comparison of Tables III and IV shows that the positions of the peptide termini and some side chains are similar to those stabilizing the extended nonamer.

TABLE III

Total interaction energy for each residue of peptide M.56-68 of the influenza matrix protein in helical conformation

| Residue No. | Type | Energy | MHC Contact residues |
|---|---|---|---|
| 56 | Phe | −94 | Y7,Y59,G62,E63,Y171 |
| 57 | Lys | −73 | Y159,T163 |
| 58 | Gly | −1 | Y7,K66,Y159 |
| 59 | Ile | 16 | K66 |
| 60 | Leu | −4 | Q155,L156 |
| 61 | Gly | 2 | R97,H114,L156 |
| 62 | Phe | −52 | F9,H70,R97,Y99 |
| 63 | Val | −43 | H70,T73,R97 |
| 64 | Phe | 6 | W147,V152 |
| 65 | Thr | −17 | R97,H114,W133,W147 |
| 66 | Leu | −20 | T73,H74,D77,R97,Y116 |
| 67 | Thr | 2 | T73,H74,D77,W147 |
| 68 | Val | −80 | K146,W147,V152 |

<sup>a</sup>CHARMm interaction energy with MHC, kcal/mol.

TABLE IV

HLA-A2/M.58–66 complex characteristics

| | | RMS from $E_{int}$<sup>c</sup> | | Side | MHC Contact |
|---|---|---|---|---|---|
| Residue | Motif | B-27<sup>a,b</sup> | Backbone<sup>d</sup> | chain | Residues<sup>e</sup> |
| 58 G | L | 1.38 | −66 (−52) | 0 | (Y7),(Y59),E63,(Y171) |
| 59 I | (M) | 0.94 | 2 | −13 | Y7,F9,M45,(K66) |
| 60 L |  | 0.74 | −3 | −10 | (H70),Y99,Y159 |
| 61 G | (E,K) | 0.74 | −9 | 0 | K66 |
| 62 F |  | 0.35 | −2.5 | −.5 | — |
| 63 V | (Y) | 0.55 | −3 | 1 | T73 |
| 64 F |  | 0.54 | −22 | 6 | T73,(R97),V152,L156 |
| 65 T | (K) | 1.08 | −18 | −7 | R97,D77,K146,(W147) |
| 66 L | V | 0.61 | −67 (−67) | −11 | (T143),D77,Y84,(Y116),(K146) |

<sup>a</sup>Backbone RMSD from an HLA-B27 bound peptide.
<sup>b</sup>Total backbone RMSD is 0.83 Å.
<sup>c</sup>Interaction energy between peptide residue and MHC, kcal/mol.
<sup>d</sup>Numbers in parenthesis are electrostatic contributions from amino and carboxyl ends of the peptide.
<sup>e</sup>Positions in parenthesis make the major contribution to the interaction energy.

For the amino terminus, 11 of the 20 most stable positions, including the six with lowest energy, were found in pocket A, close to the position the peptide amino end occupies in the x-.ray structure of the MHC allele HLA-B27. Four other, somewhat less favorable positions clustered in the vicinity of Asp-77, while the remaining five were scattered throughout the site. For the carboxyl terminal Leu, 13 of the 20 best positions were in pocket F, at a position homologous to that of the HLA-B27 location known to accommodate the carboxyl end of HLA-B27 binding peptides. The eight lowest of the 20 positions were among these 13 positions. Three other locations fell in pocket B near Lys-66. These locations were ruled out since they would reverse the orientation of the peptide in the MHC groove. The remaining four were scattered throughout the site.

The five best positions were selected for each terminal residue, and for each of the 25 combinations of positions attempted to close the chain by constructing suitable conformations for residues 2–8 using the CONGEN program. Solutions to the chain closure equations were found for 13 of the 25 pairs. Thus, some combinations of the end positions were unable to accommodate an intervening peptide segment. For each acceptable pair the five lowest energy conformations were selected from (typically) several hundred conformations that closed the chain. Of the 13×5=65 conformations, the ten lowest energy structures were selected and their CHARMm energy minimized until the potential gradient was below 0.2 kcal/mole/Å. The structures were compared to the x-ray structure of a peptide in the cleft of HLA-B27 by superimposing HLA-B27 on HLA-A2, and then calculating the RMSD between the two peptides.

The procedure included three cutoffs: (i) 5 positions for each terminal residue, (ii) the 5 best structures from each CONGEN run, and (iii) the best overall 10 structures for CHARMm minimization were retained. The final results were relatively insensitive to where the cutoffs were chosen. With respect to (i), the approximate location of the peptide termini was known from crystallographic data. The five best positions for the amino and the carboxyl ends fell within these known regions in pockets A and F, respectively. Retaining more than 5 positions would have led to choosing structures outside these pockets, and the additional positions would be necessarily rejected. Retaining fewer than 5 positions would have only a small effect on the results, because the positions within clusters were sufficiently close that each cluster could be approximately represented even by a single structure.

Figure 7:
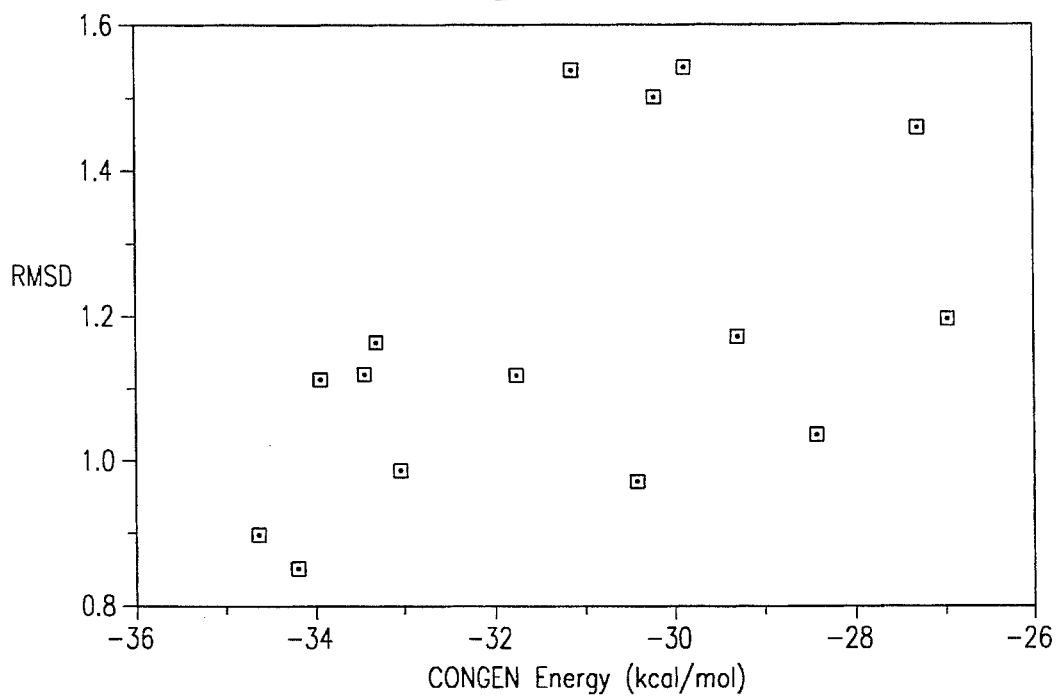
FIG. 7 depicts a comparison of the 15 best CONGEN chain closures for a single termini pair.

The cutoff (ii), i.e., the number of conformations retained after the chain closure also had only a small effect on the results, because the lowest energy conformations of the chain formed a dense cluster. The conformations were ranked in terms of $E_{int}+E_1$, the sum of the CONGEN internal energy of the peptide and peptide-MHC interaction energy. For a single pair of end-residues, the best 15 structures were ranked. A plot of the backbone RMSD from the B27 peptide vs. the observed $E_{int}+E_1$ showed that the 5 lowest energies were clearly associated with chains close to the B27 peptide (FIG. 7). The RMS distance of the backbone nitrogen and carbon atoms of the chain to the crystal structure of the B27 peptide was plotted against the CONGEN energies (chain internal energy plus chain-MHC interaction energy). The mean and the standard deviation of the RMSD values for the first 5 chains were 1.03 and 0.14 Å, respectively. The corresponding mean and standard deviation for the first 15 chains were 1.18 and 0.24 Å, respectively.

Subsequent energy minimization (500 steps with CHARMm) of the 15 peptide-MHC pairs yielded a range of energy values, −3015 to −3055 kcal/mol for the first 5, and −3008 to −3067 kcal/mol for the next 10. Although the backbones of the structures moved about 0.7 Å during CHARMm minimization, the mean of the RMS deviations from the B27 peptide remained almost unchanged, whereas the standard deviation of RMSD values was slightly reduced. There was a significant change in side chain conformations. For example, the ring of Phe-5, placed high out of the binding grove by the CONGEN search in the lowest energy structures, moved somewhat down. Thus it appeared that CONGEN was important in locating the peptide backbone. The chain closure in itself produced backbone conformations very close to the one observed in the B27 peptide.

According to (iii), the 10 best overall structures from the 65 (=5×13) selected at the previous step were then minimized extensively. The backbone RMSD of the lowest energy M.58-66 structure from the crystallized HLA-B27 peptide was 0.83 Å (Table IV). For HLA-A2, the CHARMm minimization that followed the CONGEN search, slightly increased the RMSD of the best (i.e., CONGEN lowest energy) conformation from the B27 peptide.

The structure obtained for the HLA-A2 gag 9-mer by a similar calculation had an all backbone atom RMSD from the B27 peptide of 0.97 Å (Table V).

TABLE V

HLA-A2/G.268–276 complex characteristics

| Residue | Motif | RMS from $E_{int}$[c] B-27[a,b] | Backbone[d] | Side chain | MHC Contact Residues[e] |
|---------|-------|--------|----------|------|----------|
| 266 I   | L     | 1.43   | −81 (−60)| −3   | (Y7),(Y59),E63,(Y171) |
| 267 I   | (M)   | 0.73   | −5       | −12  | Y7,F9,E63,(K66) |
| 268 L   |       | 0.69   | −18      | −5   | (H70),Y99,Y159 |
| 269 G   | (E,K) | 1.09   | 7        | 0    | K66 |
| 270 L   |       | 0.89   | 2        | −1   | — |
| 271 N   | (Y)   | 1.47   | −19      | −11  | H70,T73,(R97),F99 |
| 272 K   |       | 0.71   | 3        | −29  | (R97),V152,L156 |
| 273 I   | (K)   | 0.68   | 9        | −4   | K146,(W147) |
| 274 V   | V     | 0.57   | −58 (−50)| −12  | D77,Y84,(Y116),143),(K146) |

[a]Backbone RMSD from an HLA-B27 bound peptide.
[b]Total backbone RMSD is 0.97 Å.
[c]Interaction energy between peptide residue and MHC, kcal/mol.
[d]Numbers in parenthesis are electrostatic contributions from amino and carboxyl ends of the peptide.
[e]Positions in parenthesis make the major contribution to the interaction energy.

EXAMPLE 5

Oligopeptides: Multi-copy Application

This example describes a computational method (multi-copy) for determining the conformations induced in flexible peptides when they bind MHC receptors. The method employed a computationally efficient multiple-copy algorithm to dock the first and last residues into their corresponding pockets, then combined a multiple-copy algorithm with a bond-scaling-relaxation loop closure algorithm to determine the peptide conformation within the framework of the receptor.

The amino and carboxyl terminal residues were docked by first localizing them to cubic regions, of approximately 125 Å$^3$, that included the A and F pockets of all three structurally known human MHC receptors. Multiple random conformations and orientations of a charged carboxy-terminal residue and a charged amino-terminal residue were randomly distributed in the corresponding regions of the receptor. The potential energy of the system was then minimized using the multiple-copy mean-field approximation. The multiple copies of the ligands (docked amino acids) were transparent to each other, but each felt the full force of the MHC receptor. The receptor residues, on the other hand, moved in the mean-field of the multiple ligands. This approximation, by minimizing several amino-acid configurations simultaneously, greatly reduced the overall minimization time. Moreover, averaging the forces exerted by the multiple copies on the receptor smoothed portions of the energy surface, thus helping to avoid some local minima. Analysis of ligand clustering in a multi-copy simulation revealed previously unrecognized information on the conformational entropy of the various minima.

Figure 8A:
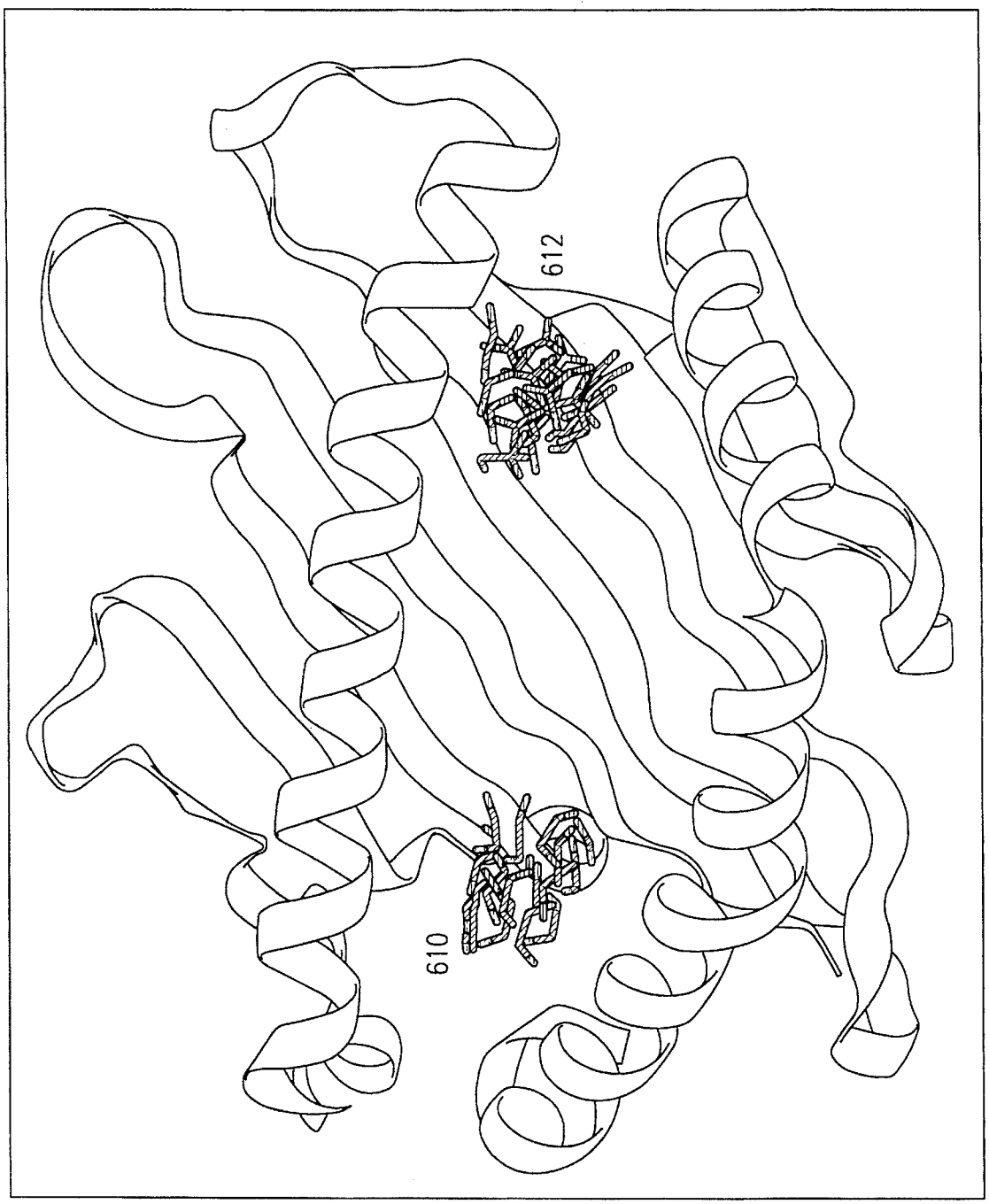
FIG. 8A represents the initial configuration.

The procedure was applied to the influenza. A matrix protein peptide 58–66 (Gly-Ile-Leu-Gly-Phe-Val-Phe-Thr-Leu), which binds to HLA-A2. During minimization the initially randomly distributed NH$_3^+$-glycines and COO$^-$-leucines (FIG. 8A) tended to cluster (FIG. 8B, FIG. 8C) and the larger clusters tended to have lower energy values. The A pocket is represented by numeral 610, and the F pocket by numeral 612. The overall movement of the ligands was large, up to 6.5 Å. In box A, two distinct clusters were observed after minimization, with 15 overlapping ligands in one cluster (the within-cluster RMSD was 0.00 Å), and 5 in the other, energetically less favorable cluster.

In pocket F, clustering was less prominent because of the larger size and the relatively weak interaction of this side chain with the receptor. The majority of the interaction came from the charged carboxyl-terminus. Nevertheless, one large cluster was observed for the carboxyl-groups (17/20 copies; within-cluster RMSD was 0.0–0.6 Å), whereas the remaining 3 copies showed no tendency to cluster.

Figure 8B:
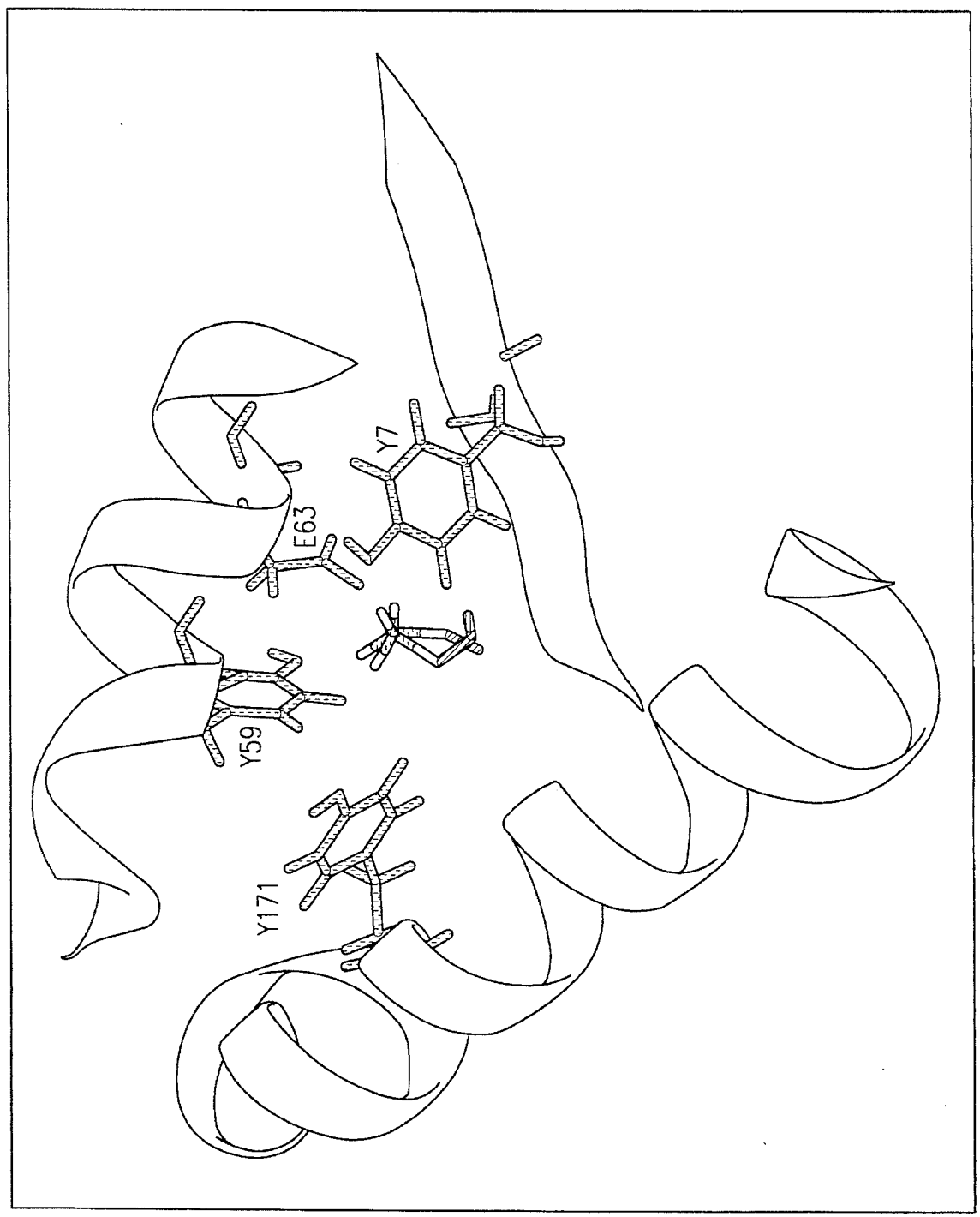
FIG. 8B depicts the final positions of N-terminal glycines.
Figure 8C:
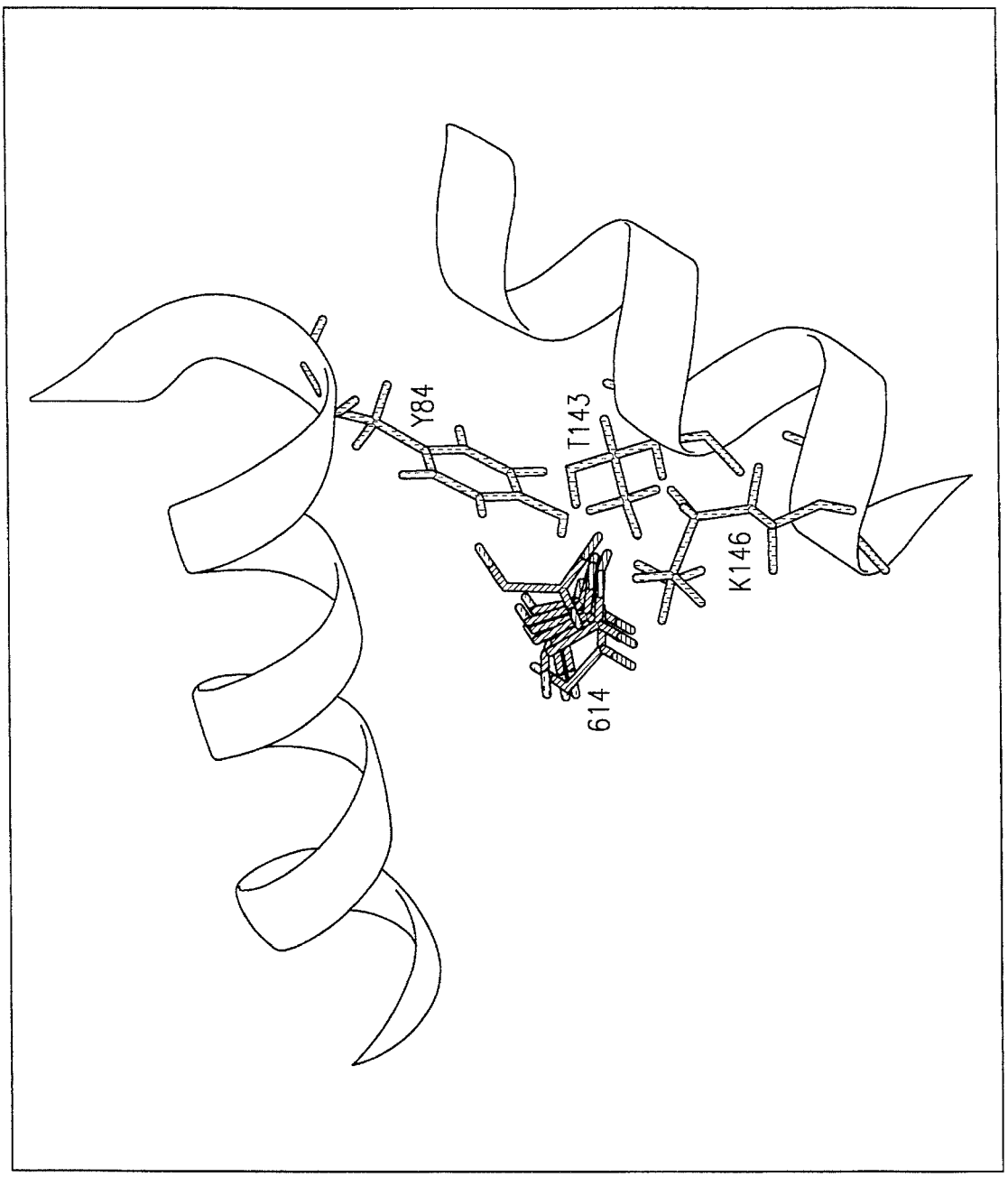
FIG. 8C depicts the final backbone positions of C-terminal leucines.

FIG. 8B shows the final positions of N-terminal glycines after multi-copy minimization. The arrow denotes 15 overlapping glycines: Receptor side chains Y171, Y59, E63 and Y7 that interacted with the docked glycines are shown. FIG. 8C depicts the final backbone position of the C-terminal leucines (numeral 614) after multi-copy minimization. The receptor side chains K146, T143 and Y84 are also shown.

Loop closure was performed using a bond-scaling-relaxation algorithm as described by Zheng, et al., *J. Comp. Chem.* 14: 556–565 (1993), and incorporated by reference herein. Briefly, random configurations were generated and subsequently scaled to meet the distance constraint, defined in this case by the two terminal residues. The equilibrium bond lengths in the empirical-energy parameters were also scaled accordingly, and the random configuration was minimized. The equilibrium bond lengths were then gradually restored, concurrent with additional cycles of energy minimization. The number of intermediate scaling-minimization cycles depended on the size of the scaling factors.

This procedure was applied in combination with the multiple-copy approach by first generating a set of 10 random loop configurations for residues 2–8 of the peptide. For backbone dihedrals only, the subspace about a largely extended conformation was sampled. Side chain dihedral angles were randomly sampled from the full dihedral-space. The backbone RMSD between the loops (after bond-scaling) was 1.0–6.0 Å. From each of these loops a group of 10 nearby loops was generated by relatively small (±10°), random perturbations of all dihedral angles, thereby further probing each of the energy basins sampled initially. The within-group backbone RMSD (after bond-scaling) was 0.4–4.8 Å. Each group of 10 copies was minimized simultaneously using the multiple-copy approximation. Because the optimal position for an isolated amino-acid will not necessarily overlap its position when it is part of a nonapeptide, the terminal residues were allowed to move during loop closure.

During loop closure the peptides tended to cluster. A cluster was defined as a group of peptides having ≦0.1 Å backbone RMSD between all peptide pairs. As with the termini, the larger clusters tended to have lower energies. Initial and final RMSDs of the peptides appeared uncorrelated. Typically, 2 or more clusters were seen after minimization (≧3 peptides/cluster), and the remaining peptides were distributed as single-copies in higher energy positions.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method for modeling the physical properties of a binding site in a receptor molecule for determining locations and conformations of amino acids in their lowest energy configurations within the binding site, comprising the steps of:

establishing X, Y, and Z coordinate axes for the receptor molecule to be modeled so that a rectangular region is established with sides parallel to the coordinate axes with the origin of the axes lying in the binding site of the receptor molecule;

establishing a grid in the X, Y, and Z coordinate axes with a grid mesh size of sufficient resolution to distinguish low-energy amino acid locations in the binding site;

scanning the binding site by placing a model amino acid at each grid point and determining the interaction energy between the amino acid and the binding site and storing in a memory that location and energy; and selecting for each amino acid the lowest energy positions in the binding site as defining the binding site for the amino acid.

2. The method of claim 1 wherein said scanning step further comprises the steps of:

prescreening the grid locations in the binding site by determining an electrostatic interaction energy between the amino acid and receptor at each grid location and amino acid orientation;

deleting the isolated low electrostatic interaction energy locations and orientations; and determining at the remaining low electrostatic interaction energy positions the amino acid-receptor configuration of lowest energy using a total potential energy process.

3. A method for modeling the minimum energy conformation of a ligand within the binding site of a receptor molecule, comprising the steps of:

establishing X, Y, and Z coordinate axes for the receptor molecule to be modeled so that a rectangular region is established with sides parallel to the coordinate axes with the origin of the axes lying in the binding site of the receptor molecule;

establishing a grid in the X, Y, and Z coordinate axes with a grid mesh size of sufficient resolution to distinguish low-energy amino acid locations in the binding site;

retrieving previously established X, Y, and Z coordinate axes for the receptor molecule and grid in the X, Y, and Z coordinate axes;

retrieving previously established low-energy amino acid configurations within the binding site;

selecting a ligand anchor pair from among the low-energy amino acid configurations consistent with the amino acid sequence of the ligand;

completing the ligand structure by closing a loop between the ligand anchor pair with amino acid residues using a loop closure process; and determining a minimum energy configuration as defining the conformations of the ligand within the receptor binding site using a molecular modeling process allowing both the ligand atoms and the receptor atoms to adjust.

4. The method of claim 3 further comprising the steps of:

selecting additional ligand anchor pairs for alternate low-energy positions and alternate amino acids within the ligand;

closing a loop between ligand pairs;

determining a minimum interaction energy for the ligand model so constructed; and selecting from all of the model ligands so constructed a model configuration of lowest total energy and storing the configuration of ligand and receptor in memory.

5. The method of claim 4 further comprising the step of displaying on a display the conformation of the binded and flexible ligand and receptor.

6. The method of claim 4 wherein the receptor is a protein.

7. The method of claim 4 wherein the receptor is a polynucleotide.

8. The method of claim 4 wherein the ligand is an oligopeptide.

9. The method of claim 4 wherein the ligand is a drug.

10. A method for modeling the physical properties of a binding site in a receptor molecule and determining the locations and conformations of end-residues of a ligand that binds to the receptor comprising the steps of:

establishing X, Y, and Z coordinate axes for the receptor molecule to be modeled so that a rectangular region is established with sides parallel to the coordinate axes with the origin of the axes lying in the binding site of the receptor molecule;

establishing a box, A, surrounding the probable, location of the amino terminus of the ligand and a box, C, surrounding the probable location of the carboxy terminus of the ligand;

placing at random positions in box A copies of a model of the amino terminus ligand residue and placing in box C copies of a model of the carboxy terminus of the ligand;

minimizing energy by a multi-copy mean-field approximation of the collection of amino termini located in box A by simultaneously moving all the charged end amino acid residue copies within box A until each copy obtains a minimum energy location;

grouping the copies of the amino terminus into clusters of similar location and configuration;

minimizing energy by a multi-copy mean-field approximation of the collection of carboxy termini located in box C by simultaneously moving all the charged end carboxy residue copies within box C until each copy obtains a minimum energy location;

grouping copies of the carboxy terminus into clusters of similar location and configuration;

selecting a representative of the amino terminus from the largest cluster in box A as defining the location and configuration of the amino terminus of the ligand;

selecting a copy of the carboxy terminus from the largest cluster in box C as defining the location and configuration of the carboxy terminus of the ligand; and storing the selected locations and configurations for the amino terminus and carboxy terminus.

11. The method of claim 10 further comprising the step of storing in a memory the conformations of the binding site and ligand.

12. A method for modeling the minimum energy conformation of a ligand within the binding site of a receptor molecule, comprising the steps of:

establishing X, Y, and Z coordinate axes for the receptor molecule to be modeled so that a rectangular region is established with sides parallel to the coordinate axes with the origin of the axes lying in the binding site of the receptor molecule;

retrieving previously established low-energy end-residues for the amino terminus and carboxy terminus within the binding site;

completing the ligand chain structure by closing a loop between the end-residues with models of amino acid residues corresponding to the ligand using torsion angles corresponding to the expected conformation of the ligand and scaling bond lengths to make the intervening chain of correct length to reach between the two end-residues;

randomly generating a set of similar loops with torsion and bond angles randomly perturbed from that of the previously constructed chain;

minimizing energy by a multi-copy mean-field approximation of the collection of model ligands by simultaneously moving all of the ligands and rescaling the bond lengths to reach known covalent bond lengths;

grouping the collection of ligands into clusters of similar location and configuration; and selecting from the largest cluster a representative defining the predicted ligand structure.

13. The method of claim 12 wherein the receptor is a protein.

14. The method of claim 12 wherein the receptor is a polynucleotide.

15. The method of claim 12 wherein the ligand is an oligopeptide.

16. The method of claim 12 wherein the ligand is a drug.

17. The method of claim 12 further comprising the step of storing in a memory the conformations of the binding site and ligand.

\* \* \* \* \*

UNITED STATES PATENT AND TRADEMARK OFFICE
CERTIFICATE OF CORRECTION

PATENT NO. : 5,495,423
DATED : February 27, 1996
INVENTOR(S) : Charles DeLisi and James L. Cornette It is certified that error appears in the above-indentified patent and that said Letters Patent is hereby corrected as shown below:

Column 8, line 28, "graphics program Par" should read --graphics program for --.

Column 10, line 61, "amino acid[ sequence." should read --amino acid sequence.--.

Column 11, line 51, "angles ,consistent" should read --angles consistent--.

Column 12, line 65, "from Arg-52, Ash-" should read --from Arg-52, Asn---.

Column 14, line 17, "groove,, toward" should read --groove, toward--.

Column 15, line 33, "6" should read -- -6 --.

Signed and Sealed this

Eighteenth Day of June, 1996

Attest:

BRUCE LEHMAN

*Attesting Officer*                *Commissioner of Patents and Trademarks*